United States Patent [19]
van Boeckel et al.

[11] Patent Number: 4,841,041
[45] Date of Patent: Jun. 20, 1989

[54] PENTASACCHARIDES AND TETRASACCHARIDES HAVING ANTI-THROMBOTIC ACTIVITY

[75] Inventors: Constant A. A. van Boeckel, Mercuriusstraat; Tom Beetz, Lith, both of Netherlands; Maurice Petitou, Paris, France

[73] Assignees: Akzo N.V., Arnhem, Netherlands; Sanofi S.A., Paris, France

[21] Appl. No.: 217,997

[22] Filed: Jul. 12, 1988

[51] Int. Cl.$^4$ .................. C08B 37/00; A61K 31/715
[52] U.S. Cl. ......................... 536/118; 536/121; 536/123
[58] Field of Search .............. 536/121, 118, 123

[56] References Cited
U.S. PATENT DOCUMENTS
4,777,161  10/1988  Lormeau et al. .................. 536/21

Primary Examiner—Ronald W. Griffin
Attorney, Agent, or Firm—William M. Blackstone

[57] ABSTRACT

The present invention is dealing with new pentasaccharides of the formula I:

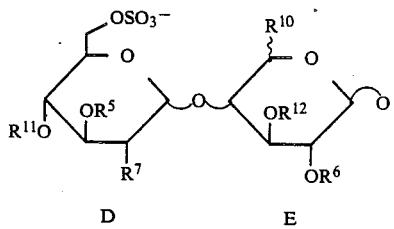
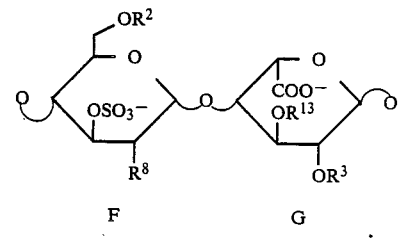
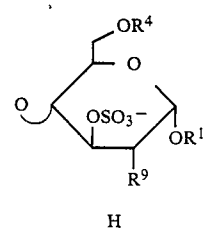

These pentasaccharides have anti-thrombotic activity and especially they possess potent anti-Xa activity, inactivate thrombin via HC-II, but do not inactivate thrombin via AT-III.

The invention also refers to new tetrasaccharides which may be used as intermediates in the synthesis of the above pentasaccharides.

10 Claims, No Drawings

PENTASACCHARIDES AND TETRASACCHARIDES HAVING ANTI-THROMBOTIC ACTIVITY

The present invention is dealing with new pentasaccharides, with a process for their preparation and with pharmaceutical compositions containing same.

The invention is also dealing with new tetrasaccharides which are valuable intermediates in the preparation of the new pentasaccharides.

More particularly the present invention is dealing with pentasaccharides of the formula:

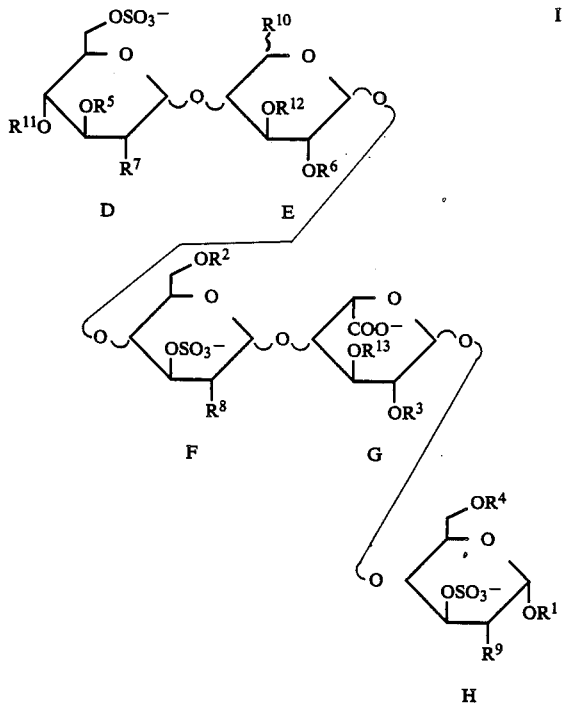

wherein:
$R^1$ is hydrogen or alkyl (1-20 C),
$R^2, R^3, R^4, R^5, R^6, R^{11}, R^{12}$ and $R^{13}$ represent hydrogen or the moiety $SO_3^-$
$R^7, R^8, R^9$ represent OH, $OSO_3^-$, $NHSO_3^-$ or NH-acyl
$R^{10}$ represents the moiety $COO^-$, $CH_2OH$ or $CH_2OSO_3^-$ and the charge of the various charged moieties is compensated by a suitable (pharmaceutically acceptable) counter-ion, which may be hydrogen but is preferable an alkali metal or earth-alkali metal ion.

These pentasaccharides have anti-thrombotic activity and especially they possess potent anti-Xa activity but do not inactivate thrombin via AT-III.

Structurally related saccharides are described in the European patent application No. 84,999. Among a variety of intermediate saccharides the above patent application also discloses biologically active polysaccharides such as penta- and hexasaccharides. The shortest pentasaccharide having potent anti-thrombotic activity is characterised by the formula:

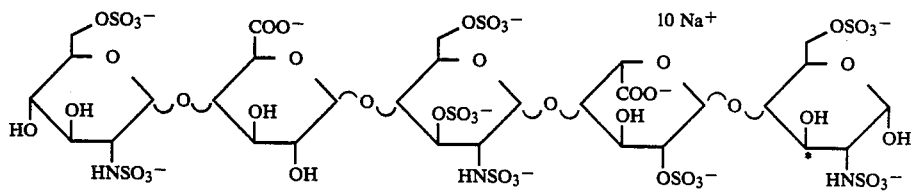

The essential difference between the pentasaccharides according to the present invention and this prior art pentasaccharide is the presence of an additional sulphate group at the position indicated by the asterisk. This extra sulphate [$SO_3^-$] moiety surprisingly increases the activation of AT-III at least by a factor of about 2, so that the presence of this sulphate group seems essential for a very potent AT-III mediated anti-$X_a$ activity and hence for potent anti-thrombotic activity. Moreover, the inactivation of thrombin via HC-II is strongly enhanced by these new pentasaccharides, and the biological half-life is significantly prolonged, resulting in a favourable anti-thrombotic profile.

The pentasaccharides according to the invention are prepared according to well known methods described and used for the synthesis of polysaccharides. In this respect a particular reference is made to the European patent application No.84,999 cited already where various methods for the synthesis of polysaccharides are disclosed.

In general, building blocks consisting of D-glucose, L-idose, D-glucosamine, D-glucuronic acid and L-iduronic acid, suitably protected at those reactive positions which are not allowed to react in the condensation-reactions, are condensed together in the correct order. Preferably, a suitably protected disaccharide corresponding to a fragment EF is activated at the anomeric center of F and then coupled to a suitably protected disaccharide corresponding to fragment GH, having a free 4-hydroxyl group at unit G resulting in the fully protected tetrasaccharide EFGH. This tetrasaccharide is subsequently deprotected selectively at the 4-hydroxyl group of unit E and then coupled with an activated and suitably protected unit D, resulting in a protected pentasaccharide DEFGH. Hydrolysis of the carboxylate moieties and the esterified hydroxyl groups results in a partially protected pentasaccharide of the formula II:

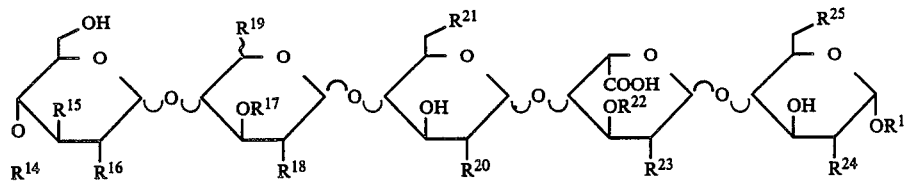

D E F G H or a salt thereof,
wherein:
$R^1$ has the meaning assigned above,
$R^{14}$, $R^{15}$, $R^{17}$, $R^{18}$, $R^{21}$, $R^{22}$, $R^{23}$ and $R^{25}$ each represent either a free hydroxyl group or the moiety OBzl,
$R^{16}$, $R^{20}$ and $R^{24}$ represent one of the moieties OH, OBzl, $N_3$, NH-acyl, or NHBzl,
$R^{19}$ represents one of the moieties —COOH, —CH$_2$OH or CH$_2$OBzl, and
Bzl represents a protecting group, preferably a benzyl group that can be removed by hydrogenolysis.

The disaccharide building block GH and the tetrasaccharide building block EFGH are, moreover, new intermediates in the synthesis of the pentasaccharide according to the invention.

The intermediate GH is characterised by the formula III

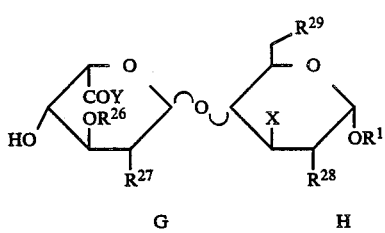

G H or a salt thereof,
wherein
Bzl and $R^1$ have the meanings indicated above,
X represents an O-acyl moiety whereby the acyl moiety can be removd by hydrolysis,
Y represents an OALK moiety, whereby ALK represents a hydrocarbon radical, preferably a lower alkyl (1–4 C) group;
$R^{26}$, $R^{27}$ and $R^{29}$ each represent a moiety selected from X and OBzl, and
$R^{28}$ represents a moiety selected from X, OBzl, $N_3$, NH-acyl or NHBzl.

The disaccharide building block GH may be prepared by coupling units G and H in an analogous manner as described already in the literature. Preferably unit G is a 2,4,6-tri-0-acyl-3-0-benzyl-α-L-idopyranose fluoride and unit H is methyl 3,6-di-0-acyl-2-benzyloxycarbonylamino-2-deoxy-α-D-glucopyranoside or methyl 2,3,6-tri-0-acyl-α-D-glucopyranoside.

A major advantage of the latter starting unit H is the fact that this compound can easily be obtained in one single step from the cheap and commercially available methyl glucoside.

The new tetrasaccharide building block EFGH is characterised by the general formula IV

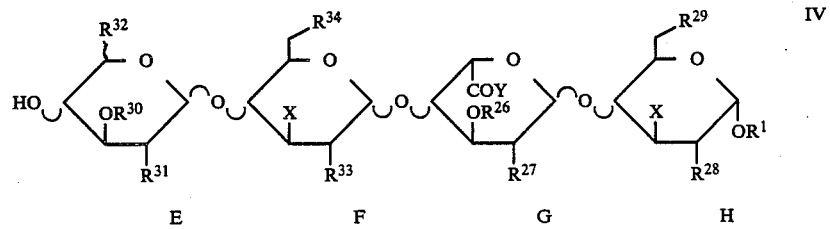

E F G H or a salt thereof,
wherein
$R^1$, Bzl, X, Y, $R^{26}$, $R^{27}$, $R^{28}$ and $R^{29}$ have the meaning indicated above
$R^{30}$, $R^{31}$ and $R^{34}$ represent the moieties X or OBzl
$R^{33}$ represents one of the moieties X, OBzl, $N_3$, NH-acyl or NHBzl and
$R^{32}$ represents one of the moieties —COY, CH$_2$X or CH$_2$OBzl.

The new tetrasaccharide intermediate may be prepared by coupling of the building block GH according to the general formula III with the activated building block EF in an analogous manner as described in European patent application No. 84,999.

With an alkyl group in the definition of $R^1$ is meant a linear or branched alkyl group with 1–20 carbon atoms, such as methyl, ethyl, propyl, butyl, isobutyl, sec-butyl, tert-butyl, pentyl, hexyl, octyl, decyl, dodecyl, pentadecyl and eikosyl.

The preferred alkyl group possesses 1–4 carbon atoms and is more preferable a methyl group.

With acyl group in the definition of $R^7$, $R^8$, $R^9$, $R^{16}$, $R^{20}$, $R^{24}$, X, $R^{28}$ and $R^{33}$ is meant an acyl group derived from an aliphatic, cycloaliphatic, araliphatic or heterocyclic aliphatic carboxylic acid with 2–20 carbon atoms, such as acetic acid, propanoic acid, hexanoic acid, decanoic acid, stearic acid, octadecanoic acid, benzoic acid, cinnamic acid, cyclohexyl carboxylic acid. Preferred acyl groups are lower aliphatic (2–6 C) acyl groups (such as acetyl and propionyl) and the benzoyl group.

The starting product according to formula II can be converted into the final pentasaccharide of formula I by the following subsequent steps:
(1) sulphation of the free hydroxyl groups,
(2) hydrogenolysis of the Bzl-protecting groups resulting in free hydroxyl groups and simultaneous hydrogenolysis of other groups such as the azido or N-benzyloxycarbonyl group(s), if present in the molecule, to the —NH$_2$ moiety, (3) sulphation of the —NH$_2$ moiety(ies) thus obtained.

In an alternative but in essence similar method, the above sequence of steps can be interchanged, viz.

(1) reduction of the azido moiety(ies) and other reducable groups—if present—resulting in (a) free amino group(s).
(2) simultaneous sulphation of both the available free hydroxyl groups and free NH$_2$ groups and
(3) hydrogenolysis of the Bzl-protecting groups.

The sulphation of a hydroxyl group is well known in the art and can be carried out for example by dissolving the product in a suitable (inert) solvent such as dimethylformamide and adding a suitable sulphating agent such as sulphur trioxide, and preferably a trimethylamine-sulphur trioxide complex.

The sulphation of an amino group (NH$_2$ group) may be carried out in the same manner, using an aqueous solution whereby an alkaline pH of the reaction mixture and preferably above pH 8 is preferred.

The hydrogenolysis of the Bzl-protecting group is carried out in a manner well known in the art and described in the chemical text books. A preferred hydrogenolysis is carried out by agitating the reaction mixture with hydrogen in the presence of a metal catalyst such as platina, palladium or palladium on charcoal.

The preferred Bzl-group is benzyl.

The azido group may be hydrogenolyzed in the same manner but may—where a simultaneous hydrogenolysis together with the Bzl-protecting group is not necessary or wanted—also be selectively converted into the NH$_2$-moiety by other reduction means such as methyl hydrids e.g. lithium aluminium hydride or sodium borohydride, or with H$_2$S in pyridine.

The compounds of the invention are preferably isolated in the form of a pharmaceutically acceptable salt, especially an alkali metal or earth-alkali metal salt, such as sodium, potassium, lithium, calcium or magnesium.

The preferred pentasaccharide according to formula I possesses whether or not in combination:

(a) an alkyl group (1–4 C) and preferably methyl for $R^1$,
(b) a sulphate moiety for $R^2$, $R^3$ and $R^4$,
(c) hydrogen or a sulphate moiety for $R^5$ and $R^{11}$,
(d) hydrogen for $R^6$, $R^{12}$ and $R^{13}$,
(e) an aminosulphate moiety (NHSO$_3^-$ moiety) for $R^8$,
(f) an aminosulphate moiety or O-sulphate moiety for $R^7$ and $R^9$, and
(g) a —COO$^-$ moiety for $R^{10}$ (D-glucuronic acid) and the saccharide is isolated in the form of its alkali metal salt, preferably the sodium salt.

The novel compounds of the invention can be employed both enterally (e.g. orally or reetally) and parenterally. For this purpose they are usually mixed with suitable pharmaceutical auxiliaries and then compounded into tablets, pills, dragees, pastilles, powders, capsules, microcapsules, suppositories, sprays (for example for intranasal administration), emulsions, suspensions or solutions.

These pharmaceutical preparations are manufactured in accordance with generally known galenical methods.

Parenteral administration is usually carried out with the aid of a syringe by means of which an emulsion, suspension or preferably a solution containing the active compound is administered subcutaneously, intramuscularly or intravenously.

The usual daily dosage, which can vary depending on the active compound used, is preferably between 0.01–20 mg/kg bodyweight for enteral administration and 0.01–10 mg/kg for parenteral administration.

For a more detailed description of the various forms of administration reference is made to the European patent application No. 84,999.

INTERMEDIATE PRODUCTS (a) Protected pentasaccharides (II)

In an analogous manner as described in the European patent application No. 84,999, the fully protected pentasaccharide 1 (i and ii) (see formula sheet A) was obtained by coupling the bromide 2a with the tetrasaccharide 3 (i and ii) after which this protected pentasaccharide was treated with aqueous solution of NaOH (4N) in a mixture of chloroform/methanol (1:6) at ambient temperature. The esterified hydroxyl groups (Ac groups) and the methylesters present in the molecule are hereby hydrolysed to obtain free hydroxyl and free carboxylate groups resulting in a pentasaccharide of formula II, in which $R^1$ is methyl, $R^{21}$, $R^{23}$ and $R^{25}$ are hydroxyl groups, $R^{24}$ is hydroxyl or the benzyloxycarbonylamino group, $R^{16}$ and $R^{20}$ are azido groups, $R^{19}$ is a carboxylate group (D-glucuronic acid) and $R^{14}$ and $R^{15}$ are benzyloxy groups.

The Rf value of the product ($R^{24}$=NHCOO-benzyl)=0,37 on SiO$_2$ using dichloromethane/methanol 8:2; $[\alpha]_D^{20} = +22.0°$ [c=1, methanol].

In an analogous manner, starting with the same tetrasaccharide 3 (i and ii), other protected pentasaccharides can be prepared by coupling with 2b, 2c and 2d.

(b) Protected tetrasaccharides (3)

The tetrasaccharides 3 (formula sheet A) are obtained by coupling the known activated disaccharide EF (4) with the new disaccharides GH (5), see formula sheet B, followed by removal of the temporary protecting group T in a manner as described in the literature e.g. European patent application No. 84,999.

(c) Disaccharides GF (5)

1. Disaccharide 5(i)

The disaccharide 5(i) was prepared from the disaccharide 6 following a protection, oxidation and esterification method as describd for analogous compounds in J. Carbohydrate Chem. 4, 293 (1985).

The preparation of 6 is outlined schematically in formula sheet C; Rf of 6 in dichloromethane/methanol (95:5)=0.32 on SiO$_2$.

2. Disaccharide 5(ii)

The preparation of 5(ii) is outlined in formula sheet (D). A mixture of fluoride 10 (3.35 g), the alcohol 14 (4.5 g) and 4 Å molecular sieves is stirred in dichloromethane at −20° C. A cooled solution of BF$_3$ etherate (0.8 eq.) is then added.

After two hours the reaction mixture is filtered. Disaccharide 15 is obtained in 89% yield after silicagel chromatography. Its $^1$H-NMR spectrum is in agreement with the chemical structue of the disaccharide.

The disaccharide 15 is subsequently converted into the disaccharide 5(i) according to the method described in J. Carbohydrate Chem. 4, 293 (1985).

EXAMPLE 1

1. Methyl O-2-azido-3,4-di-O-benzyl-2-deoxy-6-O-sulfo-α-D-glucopyranosyl-(1→4)-O-2,3-di-O-benzyl-β-D-glucopyranuronosyl-(1→4)-O-2-azido-2-deoxy-3,6-di- O-sulfo-α-D-glucopyranosyl-(1→4)-O-3-O-benzyl-2-O-sulfo-α-L-idopyranuronosyl-(1→4)-2-(benzyloxycarbonylamino)-2-deoxy-3,6-di-O-sulfo-β-D-glucopyranoside octakis sodium salt.

A solution of compound 1 (i) mentioned in "Intermediate products" ($R^{24}$=benzyloxycarbonylamino) (156 1 mg, 0.1 mmol) in dimethylformamide was stirred for 16 hours at 50° C. in the presence of sulfur trioxide-trimethylamine complex (440 mg, 3.2 mmol). The mixture was cooled and chromatographed over Sephadex LH 20 column (dimethylformamide with 0.5% triethylamine). The crude product was then dissolved in dimethylformamide (7 ml) and treated again with sulfur trioxide-trimethylamine complex (250 mg, 1.8 mmol) for 16 hours at 50° C. The reaction mixture was cooled, concentrated in vacuo to 3 ml volume and purified by gel filtration chromatography (Sephadex LH 20, dimethylformamide with 0.5% triethylamine). The product was eluted from a column of Dowex 50 WX 4 (Na+-form) with tert.butanol/water (2:3) to give pure title compound (193 mg).

Rf=0.33 (ethylacetate/pyridine/acetic acid/water; 11/7/1.6/4).

2. Methyl O-2-deoxy-6-O-sulfo-2-(sulfoamino)-α-D-glucopyranosyl-(1→4)-O-β-D-glucopyranuronosyl-(1→4)-2-deoxy-3,6-di-O-sulfo-2-(sulfoamino)-α-D-glucopyranosyl-(1→4)-O-2-O-sulfo-α-L-idopyranuronosyl-(1→4)-2-deoxy-3,6-di-O-sulfo-2-(sulfoamino)-α-D-glucopyranoside undekakis sodium salt.

A solution of compound obtained in 1. (193 mg, 0.096 mmol) in methanol (15 ml) and water (10 ml) was hydrogenated in the presence of 10% Pd/C (140 mg) for 2 days, then filtered and concentrated. A solution of the residue in water (25 ml) was hydrogenated again for 2 days using fresh 10% Pd/C (100 mg). The suspension was filtered and concentrated to give the corresponding debenzylated compound (118 mg, 81%). This crude product, dissolved in water (16 ml) was stirred for two days at room temperature in the presence of sulfur trioxide-trimethylamine complex (120 mg) and sodium carbonate (120 mg). A second and a third portion of the sulfur trioxide-trimethylamine complex and the sodium carbonate was added on the third and fifth day respectively.

The reaction mixture was concentrated to 15 ml volume and eluted from a column of Sephadex G 10 with water. The resulting product was eluted from a column of Dowex 50 WX 4 (Na+ form) with water. The crude end product was purified by ion exchange chromatography (Sephadex DEAE) using a gradient of sodium chloride (0.5→2.0M). The pentasaccharide fractions were combined and desalted on a column of Sephadex G 10 . The pure fractions were combined and lyophilized to give the pure end product (title compound) as an amorphous white powder (99 mg, 70%). $[\alpha]_D^{20}$= +38.36° (c=0.61, $H_2O$).

EXAMPLE 2

In an analogous manner as described in example 1 are prepared:

O-2-deoxy-6-O-sulfo-2-sulfoamino-α-D-glucopyranosyl-(1→4)-O-β-D-glucopyranuronosyl-(1→4)-O-2-deoxy-3,6-di-O-sulfo-2-(sulfoamino)-β-D-glucopyranosyl-(1→4)-O-2-O-sulfo-α-L-idopyranuronosyl-(1→4)-2-deoxy-3,6-di-O-sulfo-2-(sulfoamino)-α-D-glucose undekakis sodium salt.

Methyl O-2-deoxy-3,6-di-O-sulfo-2-(sulfoamino)-α-D-glucopyranosyl-(1→4)-O-β-D-glucopyranuronosyl-(1→4)-O-2-deoxy-3,6-di-O-sulfo-2-(sulfoamino)-α-D-glucopyranosyl-(1→4)-O-2-O-sulfo-α-L-idopyranuronosyl-(1→4)-2-deoxy-3,6-di-O-sulfo-2-(sulfoamino)-α-D-glucopyranoside dodecakis sodium salt.

Methyl O-6-O-sulfo-α-D-glucopyranosyl-(1→4)-O-β-D-glucopyranuronosyl-(1→4)-O-2-deoxy-3,6-di-O-sulfo-2-(sulfoamino)-glucopyranosyl-(1→4)-O-2-O-sulfo-α-L-idopyranuronosyl-(1→4)-2-deoxy-3,6-di-O-sulfo-2-(sulfoamino)-α-D-glucopyranoside decakis sodium salt.

Methyl O-2-deoxy-6-O-sulfo-2-(sulfoamino)-α-D-glucopyranosyl-(1→4)-O-β-D-glucopyranuronosyl-(1→4)-O-2-deoxy-3,6-di-O-sulfo-2-(sulfoamino)-α-D-glucopyranosyl-(1→4)-O-2-O-sulfo-α-L-idopyranuronosyl-(1→4)-2,3,6-tri-O-sulfo-α-D-glucopyranoside undekakis sodium salt.

Methyl O-2-deoxy-6-O-sulfo-2-(sulfoamino)-α-D-glucopyranosyl-(1→4)-O-β-D-glucopyranuronosyl-(1→4)-O-2,3,6-tri-O-sulfo-α-D-glucopyranosyl-(1→4)-O-2-O-sulfo-α-L-idopyranuronosyl-(1→4)-2-deoxy-3,6-di-O-sulfo-2-(sulfoamino)-α-D-glucopyranoside undekakis sodium salt.

Methyl O-2-deoxy-4,6-di-O-sulfo-2-(sulfoamino)-α-D-glucopyranosyl-(1→4)-O-β-D-glucopyranuronosyl-(1→4)-O-2-deoxy-3,6-di-O-sulfo-2-(sulfoamino)-α-D-glucopyranosyl-(1→4)-O-2-O-sulfo-α-L-idopyranuronosyl-(1→4)-2-deoxy-3,6-di-O-sulfo-2-(sulfoamino)-α-D-glucopyranoside dodecakis sodium salt.

Methyl O-2-deoxy-3,4,6-tri-O-sulfo-2-(sulfoamino)-α-D-glucopyranosyl-(1→4)-O-β-D-glucopyranuronosyl-(1→4)-2-deoxy-3,6-di-O-sulfo-2-(sulfoamino)-α-D-glucopyranosyl-(1→4)-O-2-O-sulfo-α-L-idopyranuronosyl-(1→4)-2-deoxy-3,6-di-O-sulfo-2-(sulfoamino)-α-D-glucopyranoside tridecakis sodium salt.

Methyl O-2-deoxy-3,6-di-O-sulfo-2-(sulfoamino)-α-D-glucopyranosyl-(1→4)-O-2-O-sulfo-α-L-idopyranuronosyl-(1→4)-2-deoxy-3,6-di-O-sulfo-2-(sulfoamino)-α-D-glucopyranosyl-(1→4)-O-2-O-sulfo-α-L-idopyranuronosyl-(1→4)-2-deoxy-3,6-di-O-sulfo-2-(sulfoamino)-α-D-glucopyranoside tridecakis sodium salt.

FORMULA SHEET (A)

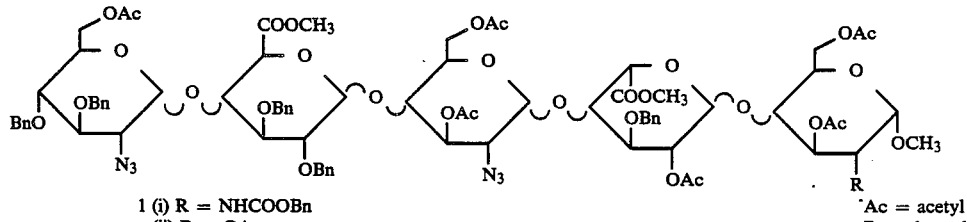

1 (i) R = NHCOOBn
(ii) R = OAc

Ac = acetyl
Bn = benzyl

-continued
FORMULA SHEET (A)
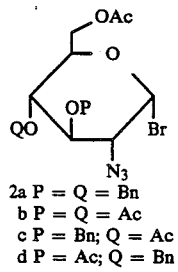
2a P = Q = Bn
 b P = Q = Ac
 c P = Bn; Q = Ac
 d P = Ac; Q = Bn
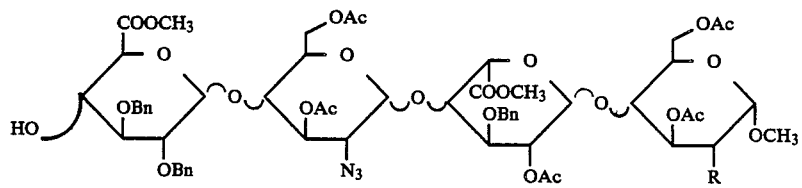
3 (i) R = NHCOOBn
  (ii) R = OAc
FORMULA SHEET (B)
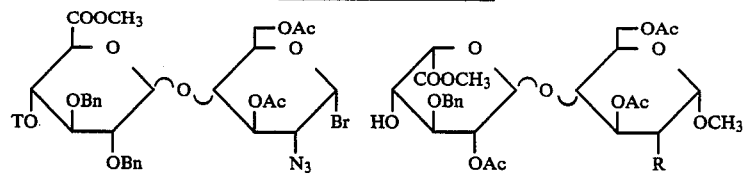
4 T = temp. protecting group
   e.g. MCA or levulinoyl
   MCA = monochloro acetyl
5 (i) R = NHCOOBn
  (ii) R = OAc
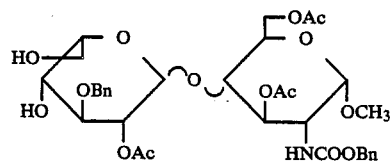
6
FORMULA SHEET (C)
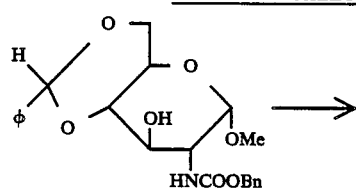
7
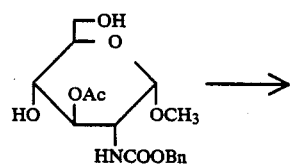
8
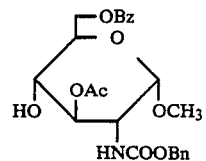
9
10
9 Bz = benzoyl
  φ = phenyl

-continued
FORMULA SHEET (C)

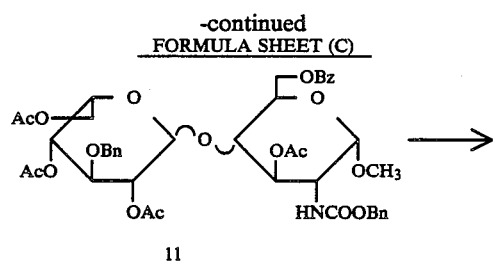

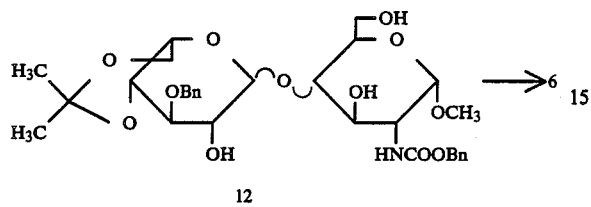

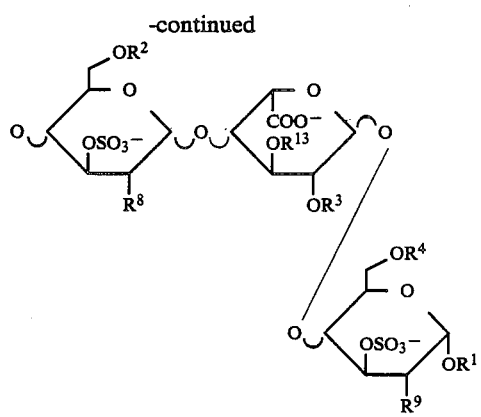

wherein:
$R^1$ is hydrogen or alkyl (1–20 C),
$R^2$, $R^3$, $R^4$, $R^5$, $R^6$, $R^{11}$, $R^{12}$ and $R^{13}$ represent hydrogen

FORMULA SHEET (D)

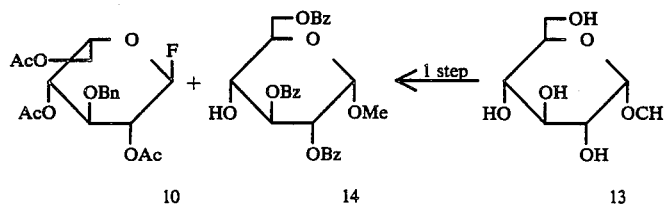

Me = methyl
Bz = benzoyl

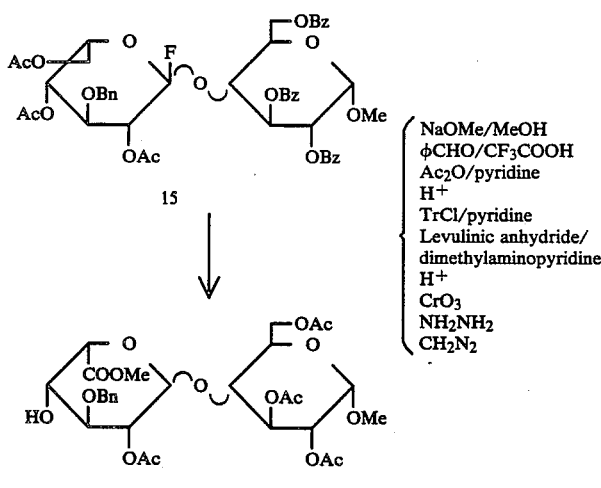

NaOMe/MeOH
φCHO/CF₃COOH
Ac₂O/pyridine
H⁺
TrCl/pyridine
Levulinic anhydride/
dimethylaminopyridine
H⁺
CrO₃
NH₂NH₂
CH₂N₂

Tr = trityl (triphenylmethyl)

We claim:
1. A pentasaccharide of the formula:

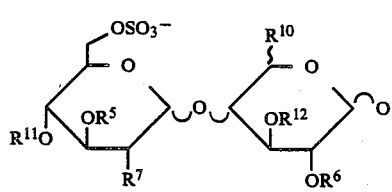

or the moiety $SO_3^-$,
$R^7$, $R^8$, $R^9$ represent OH, $OSO_3^-$, $NHSO_3^-$ or NH-acyl,
$R^{10}$ represents the moiety $COO^-$, $CH_2OH$ or $CH_2O$-$SO_3^-$ and the charge of the various charged moieties is compensated by suitable pharmaceutically acceptable counter-ions.

2. A pentasaccharide according to claim 1 in which $R^1$ represents an alkyl moiety with 1–4 carbon atoms; $R^2$, $R^3$, and $R^4$ represent the $SO_3^-$ moiety; $R^6$, $R^{42}$ and $R^{13}$ represent hydrogen;

$R^5$ and $R^{11}$ represent hydrogen or the $SO_3^-$ moiety;
$R^7$ and $R^9$ represent the $-NHSO_3^-$ or $OSO_3^-$ moiety;
$R^8$ represents the moiety $NHSO_3^-$ and
$R^{10}$ represents the $COO^-$ moiety (D-glucuronic acid configuration).

3. The pentasaccharide of claim 2, wherein $R^1$ is methyl.

4. A pentasaccharide according to claim 1 of the formula:

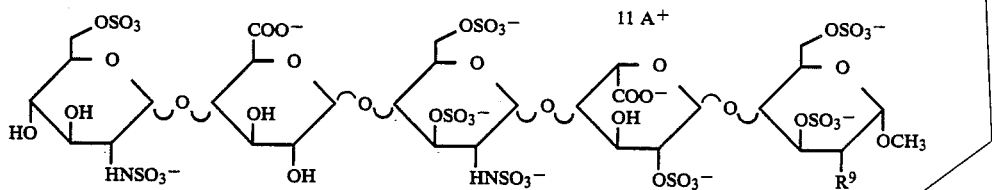

wherein A is a suitable cation and wherein $R^9$ is $NHSO_3^-$ or $OCO_3^-$.

5. Pentasaccharide according to claim 4, wherein the cation is an alkali metal.

6. A pentasaccharide according to claim 1 of the formula:

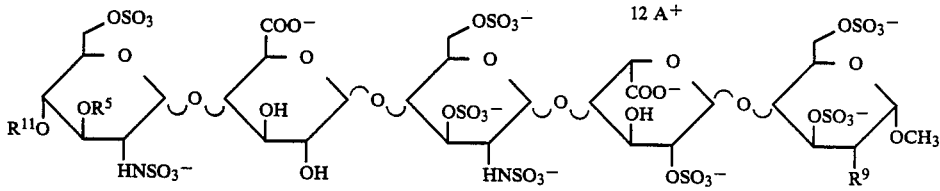

wherein A is a suitable cation and wherein $R^9$ is $NHSO_3^-$ or $OSO_3^-$, and $R^5$ and $R^{11}$ are hydrogen or the $SO_3^-$ moiety, with the proviso that $R^5$ and $R^{11}$ are not the same.

7. The pentasaccharide of claim 6, wherein the cation is an alkali metal.

8. A pentasaccharide according to claim 1 of the formula:

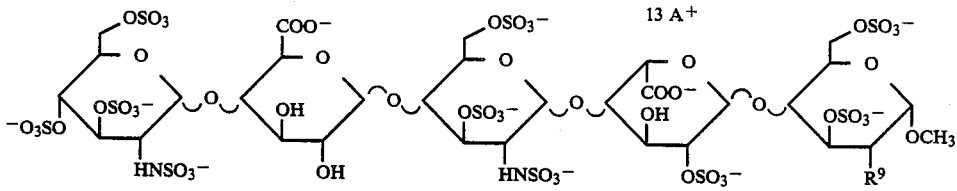

wherein A is a suitable cation and wherein $R^9$ is $NHSO_3^-$ or $OSO_3^-$.

9. The pentasaccharide of claim 8, wherein the cation is an alkali metal.

10. A tetrasaccharide of the formula:

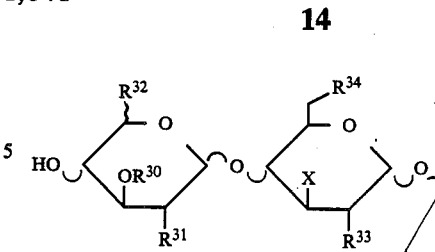

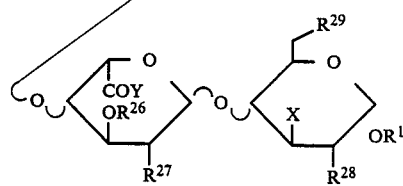

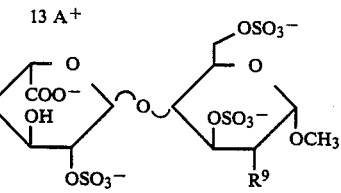

or a salt thereof, wherein
$R^1$ is H or a 1-2 C alkyl;
$R^{26}$, $R^{27}$, $R^{29}$, $R^{30}$, $R^{31}$ and $R^{34}$ represent a moiety selected from X and OBzl;
X represents an O-acyl moiety wherein the acyl can be removed by hydrolysis;
Bzl represents a protecting group that can be removed by hydrogenolysis;
$R^{28}$ and $R^{33}$ represent a moiety selected from X, OBzl, $N_3$, NH-acyl and NHBzl;
$R^{32}$ represents a moiety selected from $-COY$, $CH_2X$ and $CH_2OBzl$; and
Y represents an OALK, wherein ALK is a hydrocarbon radical.

* * * * *

UNITED STATES PATENT AND TRADEMARK OFFICE
CERTIFICATE OF CORRECTION

PATENT NO. : 4,841,041

DATED : June 20, 1989

INVENTOR(S) : Constant A.A. van Boeckel et al

It is certified that error appears in the above-identified patent and that said Letters Patent is hereby corrected as shown below:

In claim 4, line 5, delete "$OCO_3$" and substitute -- $OSO_3$ -- therefor.

Signed and Sealed this

Eighth Day of May, 1990

Attest:

HARRY F. MANBECK, JR.

Attesting Officer

Commissioner of Patents and Trademarks